United States Patent [19]

Smalley et al.

[11] Patent Number: Plant 5,335

[45] Date of Patent: Nov. 13, 1984

[54] ELM TREE CALLED REGAL

[75] Inventors: Eugene B. Smalley, Madison, Wis.; Donald T. Lester, Lake Oswego, Oreg.

[73] Assignee: Wisconsin Alumni Research Foundation, Madison, Wis.

[21] Appl. No.: 473,176

[22] Filed: Mar. 7, 1983

[51] Int. Cl.[3] ..... A01H 5/12

[52] U.S. Cl. ..... Plt./51

[58] Field of Search ..... Plt./51

*Primary Examiner*—Robert E. Bagwill
*Attorney, Agent, or Firm*—Howard W. Bremer

[57] ABSTRACT

An elm tree characterized by high resistance to the Dutch elm disease.

2 Drawing Figures

The present invention relates to a new and distinct variety of elm tree which is primarily distinguished by its high resistance to Dutch elm disease caused by *Ceratocystis ulmi.* The tree has remained symptomless in environments known to contain *Verticillium dahliae,* the causal agent of Verticillium wilt and appears to have limited susceptibility to black leaf spot disease caused by *Stegophora ulmea.*

The tree is characterized by a columnar growth habit. Soon after planting it develops a strong central leader and the young plantings require a minimum of care to maintain a strong, upright (columnar) growth habit even when subjected to partial shading. Development of older plantings (10 years) in good sites suggests a long-lined, tidy tree which will perhaps reach heights of 20 m or greater.

Foliation of the tree tends to be less dense than in the American elm with shade density resembling more closely trees such as thornless honey locust (*Gleditsia triacanthas* L.) or little leaf linden (*Tilia cordata* Mill.)

The foliation and uniform upright growth characteristics of the tree allow full lawn development while maintaining an attractive columnar habit. Thus the tree is an ideal candidate for planting in lines along drives or roads or in modern urban settings such as shopping malls and housing developments. Additionally, ice storms or severe winds have not produced injury in the parent tree under conditions causing large branch damage to *U. pumila.*

New spring growth is varleys-green in color (R#31'm) (Ridgway, 1912). As leaves mature they change to a glossy, trichome-free dusky yellowish green (R#27'''m) and then to a mature forest green (R#29'm). The lower leaf surface is a deep, dull yellow greeen (R333''k). Trichomes on the lower leaves are not prominent and are confined to the bases of the veins. Mature leaves exposed to full sun are lanceolate-ovate, unequal at the base, acuminate at the tip, doubly serrate at the leaf margins, 8–12 cm long and 3 to b 6 cm wide. The short petioles vary from 0.8 to 1.5 cm in length. Fall leaf color is not distinctive and leaves tend to be retained through several early frosts before abscission occurs. This characteristic is common in certain sources of *U. pumila* growing in south-central Wisconsin.

Apical dominance is very strong and results in limited side branching on the developing shoot of the current season's growth. Current season side branching is usually restricted to short spurs which continue subdominant growth the following season. This results in the stiff, upright growth and resulting light density foliage.

Young branches are a light brownish gray (light brown drab R#9''''b) with green showing through the bark cracks. Prominent brownish lenticels 1.3 to b 1.5 cm long form an attractive pattern on the larger branches and lower trunk of young trees. This pattern is broken at regular (2 to 2.5 cm) intervals by horizontal brownish-green bark cracks. Mature bark is a dark neutral to mouse gray (R315'''') and the substance bark is colored a light Sanford's brown (R#11k). Mature bark development occurs relatively late in the tree's life and only the basal portions of specimens at least 8–10 years old have appreciable mature bark development.

The parent tree is located in a dense planting of elm sections, and these conditions have generally retarded its growth as contrasted with other plantings on more fertile urban planting sites. The parent tree began flowering sporadically at about 15 years of age, but trees from rooted cuttings have flowered in 10 years. Floral and seed characteristics are not distinctive and most closely resemble its strong *U. carpinifolia* ancestry.

The accompanying photographs show a specimen tree of the new variety in winter and in full foliage. The specimen shown is approximately nine years old and has an approximate height of 5 meters and an approximate diameter of 20 centimeters. The columnar growth habit is readily seen from the photographs. There is no tendency for the branches nearer the base of the tree to spread and branches emanating from the trunk tend to remain relatively uniform in size.

ORIGIN

The "Regal" elm is derived from a controlled pollination of the "Commelin" elm N274 (U.×*Hollandica vegeta*×*U. carpinifolia* #1) with N215 (*U. pumila*×*U. carpinifolia hoersholmiensis*).

The hardiness (survival in Wisconsin winters) and disease resistance may be attributed in part to its 25% *U. pumila* ancestry as well as the northern (Denmark) origin of its *U. carpinifolia hoersholmiensis* grandfather.

ASEXUAL REPRODUCTION

The "Regal" elm cultivar can be propagated from root cuttings allowed to sprout in the greenhouse in moist sphagnum peat and sand. Hormone-treated sprouts can be transplanted as rooted cuttings after approximately 20 days in a perlite-peat rooting medium under fine intermittent mist. This is the preferred method of propagation. Bud-grafting has been of limited success on a range of root stocks.

DISEASE RESISTANCE

Methods for screening elm introductions and breeding progeny for DED resistance have been previously described (Smalley and Kais, 1966, in H. D. Gerold et al (eds.) Breeding Pest Resistant Trees, Pergamon Press, New York, pp. 279–292; Lester and Smalley, I.U.F.-R.O. Genetics-SABARAO Joint Symposia, Tokyo, 1972, C-5(V):1–10). In general, seedlings are grown for one year in out-door seedbeds, transplanted into field locations the second season, maintained under clean cultivation, and artificially inoculated with *Certocystis ulmi* in the 3rd and 4th year. Initial screening trials of plants from the Dutch seed lots from which "Regal" was derived utilized 10–15 different Wisconsin isolates of the pathogens. Trees were inoculated in one-year-old wood in the tree's upper crown and the inoculum contained approximately $10^6$ spores/ml. Survivors of this procedure were re-inoculated in subsequent years. As a final test (called the seasonal susceptibility test), selected resistant clones were clonally propagated in large numbers, grown in randomized field plants for one or two years, and different individuals of each clone were inoculated at 10 different times during the growing season (Table 1). In this test, the inoculum consisted of a mixed conidial suspension from 10 different isolates of the fungus from different North American locations. Observations on disease development were then recorded periodically through the year following inoculation. The cultivar herein described, named "Regal", possessed superior resistance to *C. ulmi* as shown in Tables 1 and 2.

TABLE 1

Seasonal susceptibility of selected elm clones to Dutch elm disease. Percent crown damage at final reading (7/17/74)[ab]

| Elm species[c] | Clone Number | 1973 dates of inoculation | | | | |
|---|---|---|---|---|---|---|
| | | 5/17 | 5/24 | 5/31 | 6/7 | 6/17 |
| *Ulmus americana* | 185-2 | 22.2 | 0 | 29.4 | 0 | 0 |
| | 185-4 | 33.3 | 62.5 | 33.3 | 41.3 | 11.0 |
| *Ulmus pumila* × *Ulmus japonica* | 44-26 | 0 | 0 | 0 | 0 | 0 |
| | 44-27 | 0 | 2.5 | 0 | 0.1 | 0 |
| *Ulmus hollandica* × *Ulmus pumila* | 5-2 | 82.0 | 83.8 | 90.5 | 25.5 | 38.8 |
| *Ulmus carpinifolia* | 134-2 | 6.0 | 11.1 | 12.5 | 0.1 | 8.3 |
| | 380-1 | 0.2 | 0 | 0 | 0 | 0 |
| *Ulmus pumila* × *Ulmus carpinifolia* | 196-5 | 0 | 0 | 0 | 0 | 0 |
| | 196-6 | 1.4 | 0 | 9.5 | 3 | 23.3 |
| | 196-7 | 0 | 13 | 10.0 | 15.5 | 16 |
| | 196-8 | 0.4 | 0 | 0 | 1.3 | 0 |
| Ulmus (complex[c] hybrid) 'Regal' | 228-5 | 0/3 | 0/6 | 0/3 | 0/3 | 0/4 |
| | | 6/21 | 6/28 | 7/5 | 7/19 | 8/2 |
| *Ulmus americana* | 185-2 | 0 | 0 | 0 | 0 | 0 |
| | 185-4 | 0 | 26.7 | 0 | 0 | 0 |
| *Ulmus pumila* × *Ulmus japonica* | 44-26 | 0 | 0 | 0 | 0 | 0 |
| | 44-27 | 0 | 0 | 0 | 0.1 | 0 |
| *Ulmus hollandica* × *Ulmus pumila* | 5-2 | 36.5 | 13.2 | 26.7 | 14.4 | 7.5 |
| *Ulmus carpinifolia* | 134-2 | 12.5 | 0 | 18.7 | 0.4 | 16.7 |
| | 380-1 | 1.0 | 0 | 0.2 | 0 | 0.2 |
| *Ulmus pumila* × *Ulmus carpinifolia* | 196-5 | 0 | 0.1 | 0.6 | 0.8 | 0 |
| | 196-6 | 31.8 | 7.4 | 10.0 | 0.5 | 1.3 |
| | 196-7 | 11.3 | 0 | 1.7 | 0.3 | 0 |
| | 196-8 | 0 | 1.3 | 1.5 | 1.3 | 0.6 |
| Ulmus (complex[c] hybrid) 'Regal' | 228-5 | 0/6 | 0/1 | 0/6 | 0/4 | 0/5 |

[a]Elm clones derived from trees previously symptomless following one or more inoculations with Wisconsin strains of *Ceratocystis ulmi*.
[b]Mixed inoculum from isolates of *C. ulmi* from Wisconsin, Kansas, Massachusetts, Illinois, Nebraska, Minnesota, New York, Conneticut, and Maine.
[c]Trees planted as rooted cuttings in 1971, 3 plants per clone per block, 15 clones per block, and 40 blocks (some clones incompletely represented in blocks because of transplant mortality or shortage of plants). Not all clones in the study are shown.

TABLE 2

Response of elm clones to inoculation in the field with an aggressive and a nonaggressive isolate of *Ceratocystis ulmi* and their single ascospore progeny.

| Elm species | Clone number | Crown damage (%)[a] | | | | | | | | | | |
|---|---|---|---|---|---|---|---|---|---|---|---|---|
| | | Ascospore lines | | | | | | | | | Parental | |
| | | 1 | 2 | 3 | 4 | 5 | 6 | 7 | 10 | 11 | 99[b] | 116[c] |
| *Ulmus americana* | 412-1 | 48 | 44 | 83 | 91 | 33 | 81 | 81 | — | — | 80 | 97 |
| | 411-3 | — | 27 | 78 | 78 | — | 84 | 78 | 32 | — | 95 | 99 |
| *Ulmus pumila* × *Ulmus japonica* | 44-11[d] | 0 | 0 | 0 | 0 | 0 | 0 | 0 | 0 | 0 | 0 | 0 |
| | 44-26 | 0 | 0 | 0 | 0 | 0 | 0 | 2 | — | 2 | 2 | 0 |
| | 44-27 | 0 | 0 | 0 | 0 | 0 | 0 | 0 | 0 | 0 | 0 | 0 |
| *Ulmus hollandica* × *Ulmus pumila* | 5-2 | 14 | 0 | 1 | 1 | 0 | 0 | 33 | 1 | — | 67 | 2 |
| | 5-2 | 2 | 0 | 5 | 0 | 1 | — | — | — | — | 7 | 6 |
| *Ulmus carpinifolia* | 368-2 | 37 | 0 | 19 | 25 | 0 | 15 | — | — | — | 62 | 32 |
| | 368-8 | 19 | 0 | 14 | — | — | — | — | — | — | 97 | 15 |
| | 368-10 | 25 | 2 | 24 | — | — | — | — | — | — | 95 | 17 |
| *Ulmus pumila* × *Ulmus carpinifolia* | 196-5 | 0 | 0 | — | 1 | 12 | 0 | 3 | — | — | 7 | 0 |
| | 196-6 | 0 | 0 | 0 | 0 | 0 | 0 | 0 | 0 | 2 | 5 | 0 |
| | 196-8 | 0 | 0 | 0 | 0 | 0 | 0 | 2 | 0 | — | 0 | 0 |
| Ulmus (complex[c] hybrid) 'Regal' | 228-5 | 0 | 0 | 0 | 0 | 0 | 0 | 0 | — | — | 0 | 0 |

[a]Each value is a mean of six replications (trees) inoculated in early June, 1975. Data adapted from Gkinis, 1977.
[b]Aggressive isolate-type B from Minnesota
[c]Nonaggressive isolate-type A from Maine.
[d]Sapporo Autumn Gold elm.

What is claimed is:

1. A new and distinct variety of elm tree called Regal as herein described and illustrated primarily characterized by its high resistance to Dutch elm disease and its columnar growth habit.

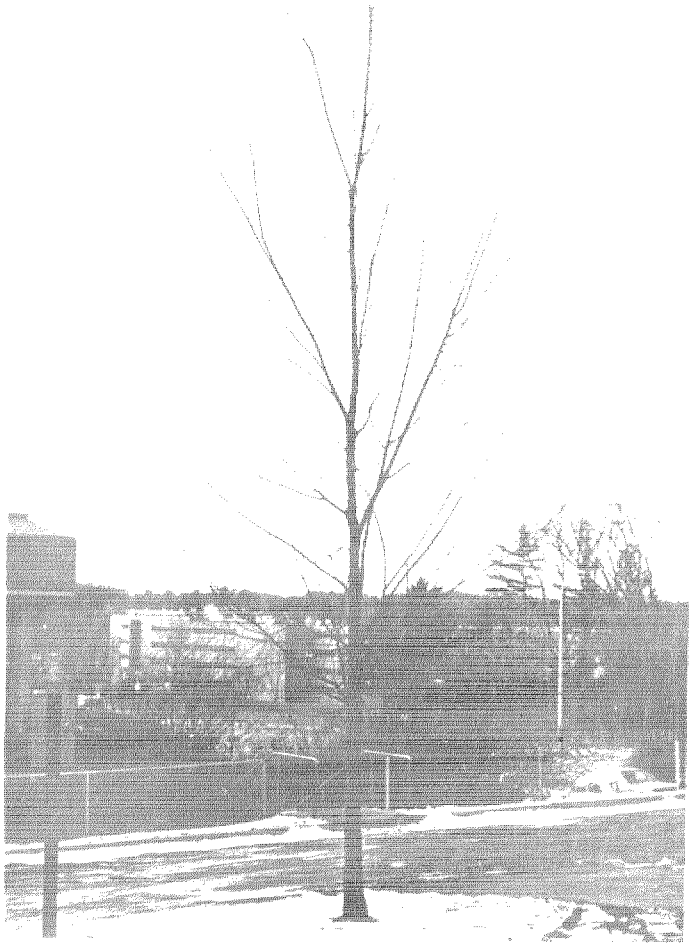

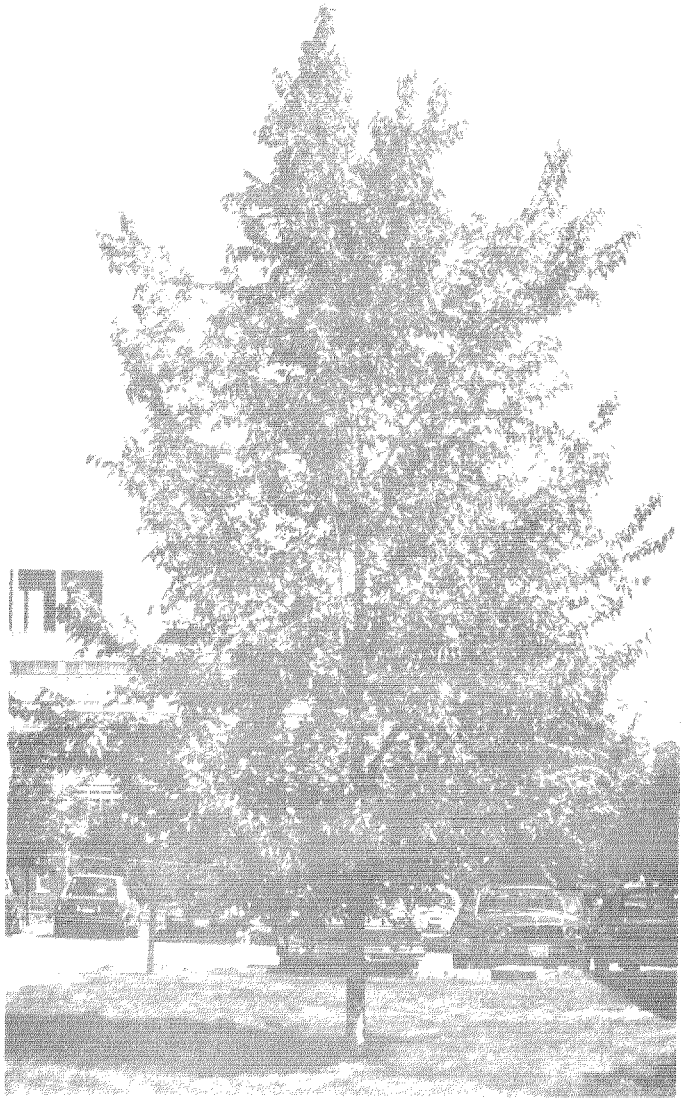

* * * * *